United States Patent [19]

Geiser et al.

[11] Patent Number: 4,755,608
[45] Date of Patent: Jul. 5, 1988

[54] PREPARATION OF 2,2'-DITHIOBIS(BENZOTHIAZOLE) IN AN ACIDIC AQUEOUS REACTING MEDIUM

[75] Inventors: Joseph F. Geiser, Uniontown; Roger J. Hopper, Akron, both of Ohio

[73] Assignee: The Goodyear Tire & Rubber Company, Akron, Ohio

[21] Appl. No.: 929,125

[22] Filed: Nov. 10, 1986

Related U.S. Application Data

[63] Continuation-in-part of Ser. No. 757,118, Jul. 11, 1985, abandoned.

[51] Int. Cl.$^4$ .......................................... C07D 417/12
[52] U.S. Cl. .................................................... 548/158
[58] Field of Search ........................... 548/158; 568/26

[56] References Cited

U.S. PATENT DOCUMENTS 2,064,395  12/1936  Tschunkur et al. ................. 548/158
2,633,447   3/1953  Head ................................. 8/127.51
4,042,319   8/1977  Baum et al. ........................... 8/634
4,337,344   6/1982  Alicot et al. ....................... 548/158

Primary Examiner—Mary E. Ceperley
Attorney, Agent, or Firm—D. O. Nickey

[57] ABSTRACT

There is disclosed a preparation of (optionally substituted) 2,2'-dithiobis(benzothiazole) by the oxidation of 2-mercaptobenzothiazole using bromate salts as the oxidant in an acidified aqueous reaction medium. The process of this invention provides an efficient and practical step in a procedure for the production of 2,2'-dithiobis(benzothiazole) that is virtually pollution free.

7 Claims, No Drawings

PREPARATION OF 2,2'-DITHIOBIS(BENZOTHIAZOLE) IN AN ACIDIC AQUEOUS REACTING MEDIUM

RELATED APPLICATIONS

This is a Continuation-in-part of Ser. No. 757,118, filed July 11, 1985, now abandoned.

TECHNICAL FIELD

This invention relates to the production of 2,2'-dithiobis(benzothiazole) which can be optionally substituted. 2,2'-dithiobis(benzothiazole) is a useful compound in the rubber industry as a vulcanization accelerator. The invention provides an improvement over the heretofore used procedures in that reaction times are reduced, and yields are improved through the use of a bromate salt that can be regenerated electrochemically to provide a pollution free process and the use of an acidified aqueous reaction medium.

BACKGROUND ART 2,2'-dithiobis(benzothiazole) or benzothiazole disulfide is marketed to the rubber industry under the tradename Altax TM by the R. T. Vanderbilt Company, Inc. Altax TM was originally developed for safe processing of rubber compounds cured at above 142° C. 2,2'-dithiobis(benzothiazole) is widely used in compounds of all types for many major commercial applications. Its activity and scorch properties can be controlled over a wide range by using various combinations of 2-mercaptobenzothiazole and ultra accelerators. As a primary accelerator 2,2'-dithiobis(benzothiazole) is non-staining and non-discoloring and imparts flat curing properties and good aging to the final rubber vulcanizate.

A presently accepted process for the production of 2,2'-dithiobis(benzothiazole) involves the use of aqueous sodium mercaptobenzothiazole, sulfuric acid and sodium nitrate. This procedure has a distinct pollution disadvantage in that sodium sulfate is formed becoming a waste water pollutant. In addition, $NO_2$ is evolved which requires an elaborate gas scrubbing system to prevent its release into the environment. The instant invention uses potassium bromate as the oxidizing agent. The resultant salts which are generated can be electrochemically oxidized back to the potassium bromate and recycled.

U.S. Pat. No. 2,064,395 relates to the preparation of organic disulfides by subjecting organic compounds that contain a sulphydryl group to the action of a compound selected from the group comprising chloric acid and salts thereof, in particular, water soluble salts such as alkali metal chlorate. The reaction of U.S. '395 is performed in an aqueous medium if desired, in the presence of acids, such as hydrochloric acid, sulfuric acid, nitric acid, phosphoric acid, formic acid or oxalic acid, and so on. The reaction takes place at ordinary temperatures and can be accelerated by the application of higher temperatures. Another feature of the '395 patent involves the use of a catalyst such as osmium tetroxide or of such substances as are capable of reducing chloric acid to a lower stage of oxidation. Such substances include nitrous acid or sulphurous acid, ferrous salts, manganous salts, cuprous salts, titanyl salts and the like. The addition of these substances has the effect that the oxidation can be performed at lower temperature or with lower concentrations of acid or that the time of the reaction can be shortened. The procedure of U.S. Pat. No. 2,064,395 requires reaction times of 4 to 30 hours and produces numerous pollutants such as the residual catalyst osmium tetroxide and molar excesses of acids.

U.S. Pat. No. 2,633,447 relates to an improved fixing composition suitable for use in processes involving changing the configuration of keratin containing substances such as hair. More particularly, this invention concerns an improved composition for use as a fixing agent in the cold permanent waving of hair. This reference discloses that alkaline metal bromates in aqueous solution are fixing agents for use in establishing disulfide linkages in reduced keratin. This reference teaches that the effectiveness is increased when the alkaline metal bromates are applied to hair in aqueous solution with acid buffers adapted to counteract the alkalinity of residual waving lotion remaining on the hair. This invention, however, does not suggest or contemplate the production of 2,2'-dithiobis(benzothiazole) via the use of aqueous acidified solutions to dramatically increase the production of 2,2'-dithiobis(benzothiazoles) from 2-mercaptobenzothiazoles.

U.S. Pat. No. 4,337,344 by Alicot et al discloses a process for the preparation of dibenzothiazyl disulfide by oxidation of mercaptobenzothiazole in aqueous suspension by means of hydrogen peroxide, in which the oxidation is effected in the presence of ethylenediaminetetraacetic acid or an alkaline metal salt derived therefrom. This patent is concerned with the production of the same material as the instant invention, however, the '344 patent does not suggest or disclose the improved process of the instant application wherein potassium bromate is utilized as an oxidizing agent in an acidified aqueous reaction medium.

U.S. Pat. No. 4,042,319 is concerned with a dye-bath oxidant comprising a mixture of bromate and iodate salts. Specifically, this patent is directed to a dye-bath oxidant for leuco sulfur or vat dyes after said dyes have been adsorbed on fibers, said oxidant consisting essentially of about 40 to 80 parts by weight of alkali bromate and about 20 to 60 parts by weight of alkali iodate, the alkali in each instance being selected from the group consisting of sodium and potassium. The '319 patent does not suggest or disclose the production of the materials of this application and further does not contemplate the use of potassium bromate as an improved oxidant in the production of 2,2'-dithiobis(benzothiazoles).

None of the prior art suggests or discloses the advantages that can be obtained in the preparation of 2,2'-dithiobis(benzothiazole) through the use of potassium bromate salts in an acidified aqueous reaction medium.

DISCLOSURE OF THE INVENTION

There is disclosed a process for the preparation of a 2,2'-dithiobis(benzothiazole) of the formula

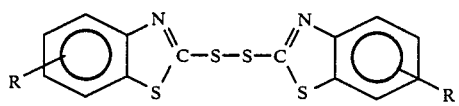

wherein R is hydrogen, an alkyl radical of 1 to 4 carbon atoms, an alkoxy radical of 1 to 4 carbon atoms, fluorine, chlorine, bromine, $NO_2$ or CN—; which comprises oxidizing a corresponding 2-mercaptobenzothiazole of the formula

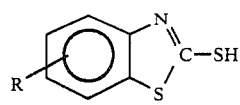

wherein R is defined as above; in an acidified aqueous solution of potassium bromate (KBrO$_3$) at a temperature of from 0-100° C.

Under specific conditions, high yields of 80-100% pure 2,2'-dithiobis(benzothiazole) are obtained from 2-mercaptobenzothiazole using KBrO$_3$ as the oxidant. Through the procedure of this invention, the pollution problems presently associated with 2,2'-dithiobis(benzothiazole) production can be eliminated in that the oxidant KBrO$_3$, after reaction, yields potassium bromide (KBr) which can be returned to the halate state by electrochemical oxidation. The halate of this invention was selected due to its ease of electrochemical formation which also requires less process control than the hypohalites presently used.

The molar ratio of 2-mercaptobenzothiazole to KBrO$_3$ can range from 1:1 to 6:1 with 6:1 being preferred. The temperature range over which the instant invention can be conducted is from 0-100° C. with 40-80° C. being preferred.

The reaction medium of this invention is weakly acidified water. By weakly acidified water is meant the use of a sufficient amount of a mineral acid to yield an initial pH of the reaction medium of less than 3.7 preferably less than 2.0. Generally, less than 1% mineral acid by weight to the weight of water has been found to be both useful and satisfactory. Mineral acids useful in the process of this invention include those mineral acids known to the skilled chemist, with HCl being the preferred acid.

The reaction is usually carried out under normal pressure, but it is also possible to carry it out in a closed reaction vessel where the pressure which builds up depends on the chosen reaction temperature.

In general, the reaction of the instant invention can be carried out by combining all the starting materials (MBT, KBrO$_3$, and acid) into a reaction vessel containing an appropriate amount of water and heating the admixture. After an appropriate amount of time and an appropriate reaction temperature, the admixture is cooled, the solids filtered therefrom and washed with water. The resulting material is dried in a circulating hot air oven at 55° C. The product obtained from the process of the instant invention is highly desirable as a vulcanization accelerator.

BEST MODE FOR CARRYING OUT THE INVENTION

The following examples are intended to illustrate the process according to the invention and are not intended to limit the same.

EXPERIMENTAL

For experimental runs 1-8 and controls 1-4, a 500 ml 4-necked reaction flask was fitted with a thermometer, a pH electrode, a condenser, a Claisien adapter and an addition funnel. A heating mantle was used to heat the mixture and a stirring shaft with a Teflon TM blade was used for mixing. To the reaction system described was charged the 2-mercaptobenzothiazole, potassium bromate, water and and HCl, when used. After the reaction was conducted as described, the mixture was cooled and the solids filtered. The collected compound was washed with water and dried in a circulating air oven. Table I sets forth the information for the seven experimental examples and Table II sets forth the data for the three comparatives.

TABLE I

Oxidation of 2-Mercaptobenzothiazole (MBT) to Altax TM with KBrO$_3$

| | REACTANTS | | | | | REACTION CONDITIONS | | | | | PRODUCT | |
|---|---|---|---|---|---|---|---|---|---|---|---|---|
| Exp. | MBT Mole | KBrO$_3$ Mole | [MBT]: [KBrO$_3$] | H$_2$O ml | HCl ml(N) | Rxn. Time hrs. | Temp. °C. | pH | Wt. g. | Yield % | mp. °C. | HPLC ratio* MBT/Altax TM |
| 1 | .0125 | .005 | 2.5 | 30 | 0.05 (12) | 4 | 24 | — | — | — | 163-168 | 0/100 |
| 2 | .125 | .05 | 2.5 | 200 | 0.03 (12) | 2.3 | 24-95 | — | — | — | 164-168 | 9/91 |
| 3 | .0625 | .025 | 2.5 | 200 | 0 | 1.5 | 50 | 6.3-3.7 | — | — | — | 97/3 |
| 3(a)** | | | | | 6.0 (0.1) | 2.0 | 50-60 | 3.7-2.8 | — | — | 176-179 | 6/94 |
| 4 | .075 | .0125 | 6.0 | 100 | 0.75 | 1.5 | 30-32 | 1.3-1.7 | 12.2 | 98.0 | 140-170 | 69.1/30.9 |
| 5 | .075 | .0125 | 6.0 | 100 | 1.0 (12) | 1.0 | 30-30 | 1.2-1.6 | 11.8 | 94.0 | 147-172 | 29.5/70.5 |
| 6 | .075 | .0125 | 6.0 | 100 | 1.0 (12) | 1.5 | 30-38 | 1.3-1.6 | 11.7 | 93.3 | 146-158 | 20.8/79.2 |
| 7 | .075 | .0125 | 6.0 | 100 | 1.0 (12) | 1.5 | 60-62 | 1.5-1.7 | 11.7 | 93.3 | 162-170 | 7.7/92.3 |
| 8 | .075 | .0125 | 6.0 | 100 | 1.0 (12) | 1.5 | 60-62 | 1.9-1.7 | 12.0 | 96.0 | 170-174 | 0/100 |

*The reaction was followed by High Pressure Liquid Chromatography (HPLC) to determine the ratio of MBT to Altax TM during the course of the reaction.
**Exp. 3 was run for 1.5 hours after which a very small amount of product was produced; then 6.0 ml of 0.1 N HCl was added. Exp. 3(a).

TABLE II

Comparatives with NaClO$_3$+

| | REACTANTS | | | | | REACTION CONDITIONS | | | | PRODUCT |
|---|---|---|---|---|---|---|---|---|---|---|
| Comp. Exp. | MBT Mole | NaClO$_3$ Mole | [MBT]: [NaClO$_3$] | H$_2$O ml | 12NHCl ml | Rxn. Time hrs. | Temp. °C. | pH | HPLC Ratio* MBT/Altax TM | mp. °C. |
| 1 | .0125 | .0108 | 1.157 | 30 | .05 | 5 | 50 | — | 96/4 | 142-161 |
| 1 (a) | | | | | | 15 | 24 | — | 96/4 | 142-160 |
| 2** | .0625 | .05 | 1.25 | 150 | .05 | 4 | 40 | — | 95/5 | — |
| 3 | .075 | .0125 | 6.0 | 100 | 1.0 | 1.5 | 30-31 | 1.3-1.3 | 97.7/2.3 | 162-178 |
| 4 | 0.75 | .0125 | 6.0 | 100 | 1.0 | 1.5 | 60-61 | 1.6-1.6 | 96.3/3.7 | 160-178 |

+Oxidant of U.S. Pat. No. 2,064,395
*Exp. 3 was run for 1.5 hours after which a very small amount of product was produced; then 6.0 ml of 0.1 N HCl was added. Exp. 3(a).
**.27 mmol V$_2$O$_5$ added at start of reaction as a catalyst From Table I it is quite evident that the use of potassium bromate in this reaction provides excellent yields at moderate reaction temperatures in a very short reaction time. This information can be compared to Table II wherein the sodium chlorate of U.S. Pat. No. 2,064,395 takes much longer in reaction time to yield an inferior product.

Direct comparisons between Example 6 of Table I and Comparative Example 3 of Table II amply demonstrates the surprising result obtained when KBrO$_3$ is used as the oxidant in place of the prior art NaClO$_3$.

INDUSTRIAL APPLICABILITY

Through the process of the instant invention, the highly desirable rubber chemical 2,2'-dithiobis(benzothiazole) can be produced efficiently and in a practical manner as part of a process that avoids the heretofore accepted slow reaction rates and attendant pollution problems. As one skilled in the art can readily appreciate, a new synthesis for this highly desirable material will fulfill a long-felt need.

We claim:

1. A process for the preparation of a 2,2'-dithiobis(benzothiazole) of the formula

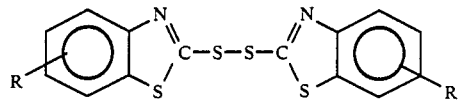

wherein R is hydrogen, an alkyl radical of 1 to 4 carbon atoms, an alkoxy radical of 1 to 4 carbon atoms, fluorine, chlorine, bromine, NO$_2$ or CN—; which consists of oxidizing a corresponding 2-mercaptobenzothiazole of the formula:

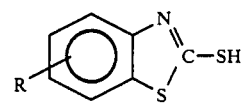

wherein R is as defined above; in an acidified aqueous solution of potassium bromate (KBrO$_3$) with a pH of less than 3.7 at a temperature of from 30–100° C.

2. A process according to claim 1 wherein R is hydrogen and the temperature of reaction is 40–80° C.

3. A process according to claim 1 wherein the molar ratio of 2-mercaptobenzothiazole to KBrO$_3$ averages from 1:1 to 6:1.

4. A process according to claim 1 wherein the aqueous solution is acidified to a pH of less than 2.0.

5. A process according to claim 1 wherein R is hydrogen and the molar ratio of 2-mercaptobenzothiazole to KBrO$_3$ is 6:1.

6. A process according to claim 1 wherein the temperature of the reaction is 50–70° C.

7. A process according to claim 1 wherein the pH of the aqueous solution is less than 2.0 and the acid is HCl.

* * * * *